United States Patent [19]

Kobayashi et al.

[11] Patent Number: 4,984,895
[45] Date of Patent: Jan. 15, 1991

[54] COLOR COMPARISON DEVICE HAVING A BULGED INSERTION GROOVE FOR HOLDING A TEST STICK IN A FLEXED CONDITION

[75] Inventors: Toshiyuki Kobayashi; Shigeru Makita, both of Kyoto; Hiroyuki Ota, Osaka, all of Japan

[73] Assignee: Omron Tateisi Electronics Co., Kyoto, Japan

[21] Appl. No.: 322,427

[22] Filed: Mar. 13, 1989

[30] Foreign Application Priority Data

Mar. 14, 1988 [JP] Japan ............................. 63-34116[U]

[51] Int. Cl.⁵ .............................................. G01J 3/52
[52] U.S. Cl. ............................................ 356/423; 422/58
[58] Field of Search ................. 356/42, 421, 422, 423, 356/424; 422/55, 56, 57, 58, 61

[56] References Cited

U.S. PATENT DOCUMENTS

| 1,617,459 | 2/1927 | Roderick | 356/42 |
| 1,631,553 | 6/1927 | Roderick | 356/42 |
| 4,509,859 | 4/1985 | Markart et al. | 356/243 |
| 4,780,283 | 10/1988 | Meinecke et al. | 422/56 |
| 4,797,256 | 1/1989 | Watlington, IV | 422/56 |
| 4,871,258 | 10/1989 | Herpichboehm et al. | 356/423 |

Primary Examiner—F. L. Evans
Attorney, Agent, or Firm—Dickstein, Shapiro & Morin

[57] ABSTRACT

A color comparison device comprises a casing unit having a comparison window for displaying a comparison color sample section mounted on a rotatable wheel and a test stick insertion groove portion formed in an upper surface of the casing unit at one end thereof and disposed generally centrally of the width of the casing unit, the insertion groove portion communicating with the comparison window so that a test stick inserted into the insertion groove portion overlies the comparison color sample section in the comparison window, the insertion groove portion having a bulged fixing section by which a test stick inserted in the insertion groove is held therein in a flexed condition.

1 Claim, 3 Drawing Sheets

COLOR COMPARISON DEVICE HAVING A BULGED INSERTION GROOVE FOR HOLDING A TEST STICK IN A FLEXED CONDITION

BACKGROUND OF THE INVENTION a. Field of the Invention

This invention relates to a test sample color comparison device used in biochemical examinations such as urine sugar, blood sugar, urobilin and other such examinations. The color comparison device contains a plurality of color reference shades which are sequentially compared to a color of a test stick reagent portion which has been impregnated, for example, with blood, in order to determine which of the color reference shades best matches the color of the reagent portion. The color shade which best matches the color of the test paper provides an indication of a biochemical condition, for example, the amount of sugar in the blood.

b. Discussion of Related Art

FIG. 3 (perspective view) and FIG. 4 (cross-sectional view) show a color comparison device on which the present invention improves. Specific details of this device are disclosed in Japanese Application No. 62-310246 and U.S. application Ser. No. 268,561 filed Nov. 8, 1988, the disclosure of Ser. No. 268,561 is incorporated herein by reference.

Another related color comparison device is also disclosed in U.S. application Ser. No. 224,367 filed July 26, 1988, the disclosure of which is also incorporated herein by reference.

The color comparison device of FIGS. 3 and 4 comprises a casing unit 1 which includes: an insertion section in the form of a test stick insertion groove portion 13 for removably receiving a color test paper portion 51 of a test stick 5: a protruding display section 11 for displaying the results of a color comparison; a manipulable rotatable wheel 2 rotatably fitted on the protruding display section 11 of the casing unit 1; a comparison color sample section 21 attached to the upper surface of the manipulable wheel 2 and having a plurality of staged reference color shades arranged in a circular array; a plurality of converter switches K mounted on the casing unit 1 in registry with the wheel 2 which convert the results of a visual comparison between the comparison color sample section 21 and the color test paper portion 51 into electrical signals representing the color shade on the wheel 2 which best matches the color of the test paper portion 51; an uneven patterned code section 4 integrally mounted on the underside of the wheel 2 and having an uneven pattern (defined by thickened portions 41 and thinned portions 42) corresponding to the staged color shades of the comparison color sample section 21 so as to operate the converter switches K as wheel 2 rotates; and a display means 14 (composed of a CPU and other electronic components) for displaying in a display section 17 the significance represented by the color shade which best matches the test paper portion 51 as designated by the converter switches K.

When a test sample color comparison is to be carried out using the above color comparison device, the test stick 5 is inserted into the stick insertion groove portion 13. In this condition, the color test paper portion 51, passed through a stick insertion inlet portion 35, is viewed through a comparison window 33 and overlies the comparison color sample section 21 of wheel 2 in registry therewith. In this condition, the manipulable wheel 2 is angularly moved (rotated) so that the color of the color test paper portion 51 can be visually compared with the staged color shades on the color sample section 21 as wheel 2 rotates to determine which color shade is the closest to the color of the test paper portion 51. As the wheel 2 is rotated, the comparison color sample section 21 underlying the color test paper portion 51 is also rotated as is underlying uneven patterned code section 4, mounted on the underside of the wheel 2, so that the plurality of converter switches K underlying the uneven patterned code section 4 in registry therewith are turned on or off in accordance with rotation of wheel 2. As a result, an electrical signal representative of the selected color shade which underlies the test paper portion 51 at any given time is generated by the converter switches K so that a signal representing the selected color shade which then underlies and best matches the color of the test paper portion 51 is generated in accordance with the states (ON or OFF) of the converter switches K. The significance (for example, the amount of blood sugar) of the selected color shade is displayed in the display section 17 through a memory means which stores the significance of the color shades for different angular positions of wheel 2, as determined by the electrical signals generated by converter switches K.

In the color comparison device of FIGS. 3 and 4, a stick insertion groove portion 13 of predetermined depth is provided in the upper surface of the casing unit 1 at one end portion thereof at a position centrally of the width of casing unit 1. The stick insertion groove portion 13 communicates with the comparison window 33, through which the comparison color sample section 21 can be viewed, through the stick insertion inlet portion 35 which is provided at one end of a cover unit 3 fitted on the casing unit 1. The cover unit 3 contains a window 34 for viewing display 17. The bottom surface of the stick insertion groove portion 13 is flat as shown in FIG. 4 and lies flush with the upper surface of the comparison color sample section 21. Therefore, when the test stick 5 is inserted into the stick insertion groove portion 13, with the color test paper portion 51 provided at the leading end portion, the leading end passes through inlet portion 35 and becomes vertically registered with the comparison window 33; that is, the color test paper portion 51 is disposed over the upper surface of the comparison color sample section 21, and the test stick 5 is disposed horizontally.

In this inserted condition of the test stick 5, it is disposed horizontally in a space between the cover unit 3 and the comparison color sample section 21, but it is not held or fixed to the display device. It has been found that this arrangement may suffer from disadvantages in use, one such disadvantage being that if the casing unit 1 is tilted during the color comparison operation, the test stick 5 can be accidentally disengaged from the casing unit 1.

SUMMARY OF THE INVENTION

It is therefore an object of this invention to provide a color comparison device which overcomes the above difficulty and can be handled more conveniently without suffering from an accidental disengagement of a test stick from a casing unit.

This object has been achieved by a color comparison device comprising a casing unit having a comparison window for displaying a rotatable comparison color sample section, a display window for displaying the results of the color comparison; a test stick insertion groove portion formed in an upper surface of the casing unit at one end portion thereof and disposed generally centrally of the width of the casing unit, with the insertion groove portion communicating with the comparison window, and with the stick insertion groove portion having a bulged fixing section by which a test stick when inserted in the insertion groove portion is inserted in a flexed condition so that it is held by its flexure in the insertion groove and to the display device.

In this color comparison device, the stick insertion groove portion communicates with the comparison window through a stick insertion inlet portion which is provided at one end of a cover unit fitted on the casing unit and having the display window and the comparison window. The stick insertion groove portion has the bulged fixing section at its proximal and from which the test stick is to be introduced into this groove portion. By virtue of the provision of this bulged section, the stick insertion groove portion is the highest at the proximal end. With this arrangement, the peak of the bulged section is at a level considerably higher than the upper surface of the comparison color sample section. Therefore, when the test stick is to be inserted into the stick insertion groove portion, the test stick is inserted in an inclined condition because of the provision of the bulged section at the proximal end of this groove portion, and the distal end portion of the test stick is passed through the stick insertion inlet portion, so that the color test paper portion of the test stick is brought into registry with the comparison window. When the distal end of the test stick is inserted into the stick insertion inlet portion, the test stick is urged downwardly, so that the test stick is flexed.

The test stick is usually made of a sheet of a plastics material, and therefore the test stick, when flexed produces a restoring force. This restoring force is borne at two points, one is the peak of the bulged section and the other is the stick insertion inlet portion, and the test stick is fixed in a flexed condition. Therefore, the test stick in its inserted and flexed condition will not be accidentally disengaged from the device body even when the body is held or positioned in different orientations, thus providing for a more convenient use.

BRIEF DESCRIPTION OF THE DRAWINGS

The above objects advantages and features of the invention will be better understood from the following detailed description provided with the reference to the accompanying drawings in which.

DETAILED DESCRIPTION OF THE INVENTION

Figure 1:
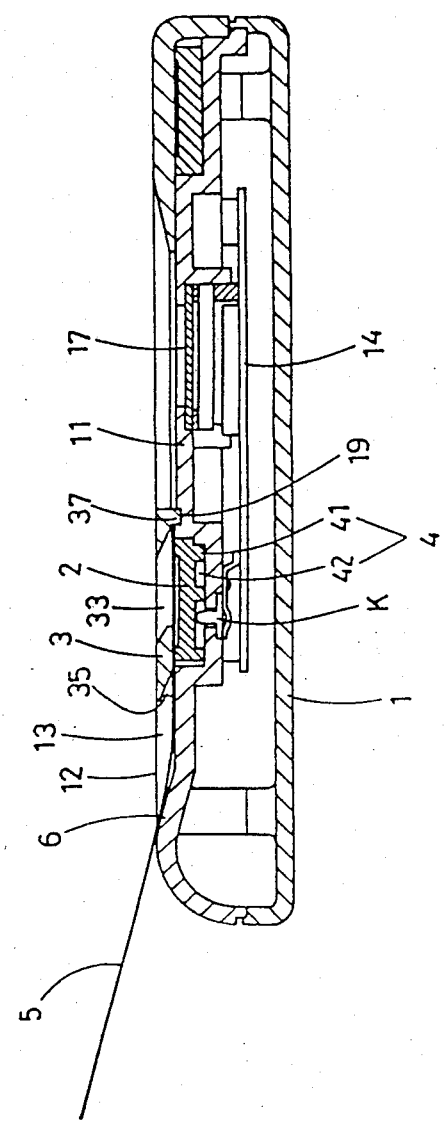
FIG. 1 is a cross-sectional view of a color comparison device embodying the present invention.
Figure 2:
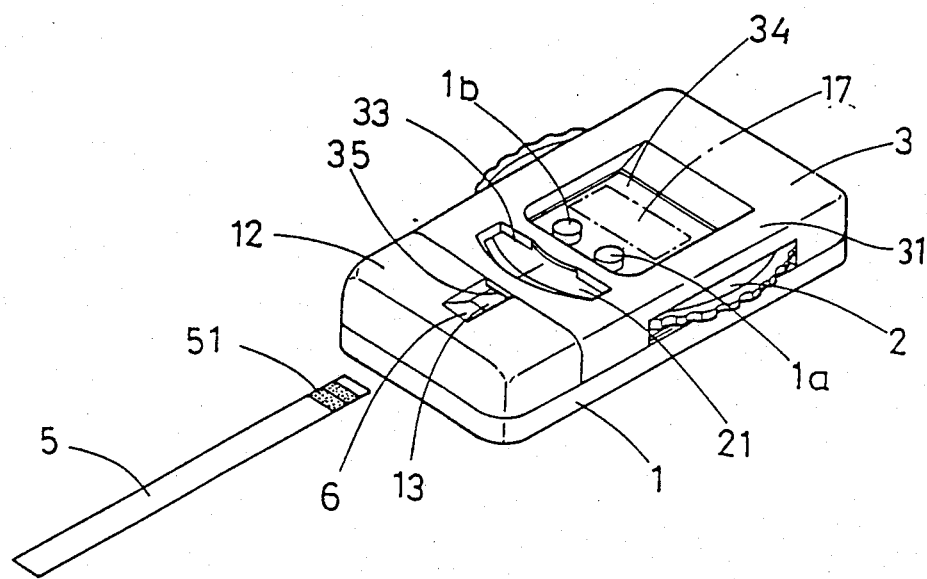
FIG. 2 is a perspective view of the color comparison device.

FIG. 2 is a perspective view of a preferred embodiment of a color comparison device of the present invention, and FIG. 1 is a cross-sectional view thereof.

Figure 3:
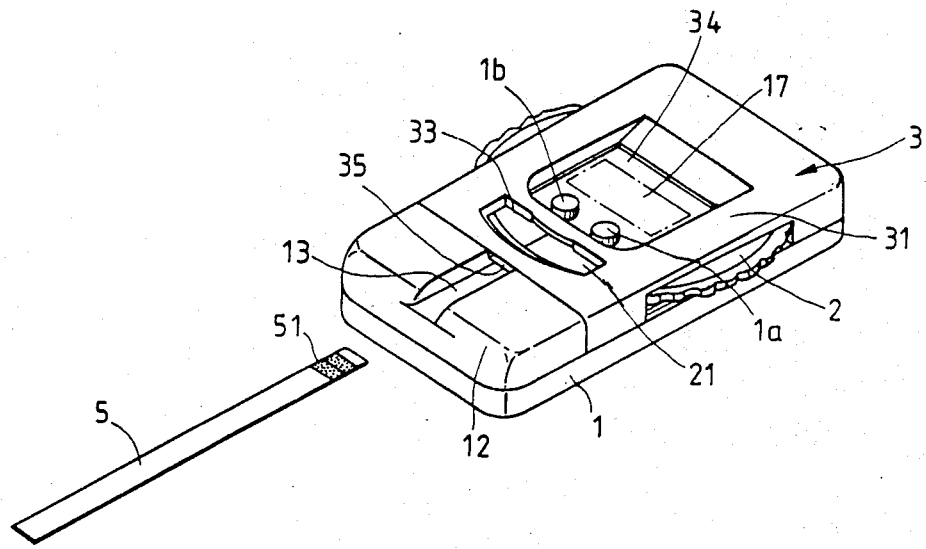
FIG. 3 is a perspective view of a color comparison device upon which the present invention improves.
Figure 4:
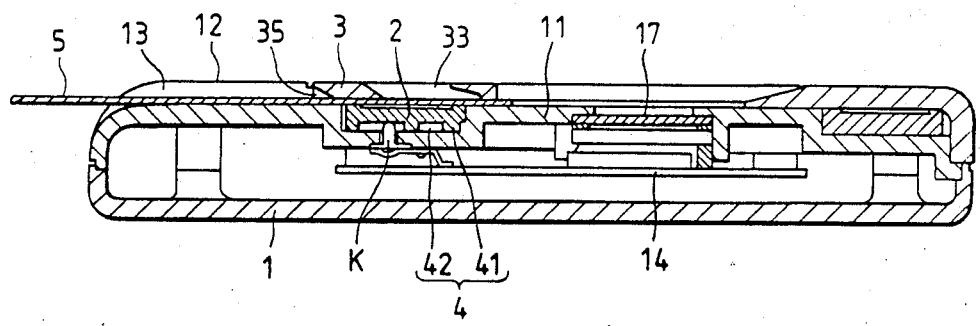
FIG. 4 is a cross-sectional view of the device of FIG. 3.

This color comparison device is generally similar in construction to the color comparison device shown in FIGS. 3 and 4 and similar parts are designated by the same reference numbers. More specifically, the color comparison device of the invention comprises a casing unit 1 which includes an insertion section (stick insertion groove portion) 13 for removably receiving a color test paper portion 51 of a test stick 5, and a protruding display section 11 for displaying the results of the color comparison. A manipulable wheel 2 is rotatably fitted on the protruding display section 11 of the casing unit and a comparison color sample section 21 is attached to the upper surface of the manipulable wheel 2 and has a plurality of staged reference color shades arranged in a circular array. A plurality of converter switches K are mounted on the casing unit 1 in registry with the wheel 2 so as to convert the results of a visual comparison, as wheel 2 is rotated, of the comparison color sample section 21 which best matches the color test paper portion 51 into electrical signals.

An uneven patterned code section 4 is integrally mounted on the underside of the wheel 2 and has an uneven pattern (defined by thickened portions 41 and thinned portions 42) corresponding to the staged color shades of the comparison color sample section 21 so as to operate the converter switches K. A display means 14 (composed of a CPU, memory and other electronic components) is also provided for displaying in a display section 17 the significance represented by the color shade then underlying the test paper portion 51, as designated by the converter switches K.

The display means determines, using a central processing unit (CPU), which color shade is in registry with the test paper portion 51 by the electrical signals generated by converter switches K and uses the electrical signals to retrieve from a memory a display value corresponding thereto which represents a biochemical condition, e.g., the amount of sugar in the blood. This value is then displayed to an operator.

A feature of the present invention resides in the fact that a bulged fixing section 6 is formed on the stick insertion groove portion 13 provided at one end of the casing unit 1 by which bulged section the test stick 5 is inserted in the stick insertion groove portion 13 in a flexed condition.

As seen from FIG. 2 which is the cross-sectional view, the casing unit 1 comprises a hollow body of a flat rectangular shape housing an electronic circuitry portion 14 comprising a power source, the CPU, the memory, etc., the casing unit 1 having the protruding display section 11 at a central portion of the upper surface thereof and also having a protruding platform 12 at one end portion thereof. The stick insertion groove portion 13 is defined by a recess formed in the upper surface of the protruding platform 12 and extending centrally of the width thereof. The cover unit 3 is fitted on the upper portion of the casing unit 1, and has a flat section 31 which has a manipulable display window 34 formed therethrough and disposed in registry with the protruding display section 11, and a comparison window 33 formed through the flat section 31 and disposed in registry with the comparison color sample section 21. A stick insertion inlet portion 35 defined by a recess is provided at insertion groove portion 13. The stick insertion groove portion 13 communicates with the comparison window 33 through the stick insertion inlet portion 35. The test stick 5 is inserted into the stick insertion groove portion 13 to reach the comparison window 33 through the stick insertion inlet portion 35. In this inserted condition, the leading or distal end portion of the test stick 5 is disposed in a space formed between the cover unit 3 (i.e., the upper wall of the insertion inlet portion 35) and the upper surface of the comparison color sample section 21.

The stick insertion groove portion 13 has the bulged section (bulged fixing section) 6 at its inlet side or proximal end portion from which the test stick 5 is to be introduced into the groove portion 13, the bulged section 6 being upwardly curved. Because of the provision of the bulged section 6, the stick insertion groove portion 13 is the highest at its inlet side and gradually slants downwardly toward the stick insertion inlet portion 35. That portion of the insertion groove portion 13 extending from the stick insertion inlet portion 35 to the comparison color sample section 21 is flat (horizontal), as is the case with the conventional stick insertion groove portion of the device shown in FIGS. 3 and 4.

The cover unit 3 has a stopper projection 37 formed on the lower surface thereof adjacent to a rear end of the comparison window 33 remote from the stick insertion inlet portion 34, and a receptive portion 19 in the form of a recess for receiving the stopper projection 37 is formed in the upper surface of the casing unit 1. Thus, the stopper projection 37 fitted in the receptive portion 19 limits a depth or length of insertion of the test stick 5 between the cover unit 3 (the comparison window 33) and the casing unit 1 (the comparison color sample section 21). In other words, the stopper projection 37 is so positioned that the color test paper portion 51 of the inserted test stick 5 can be located in vertical registry with the color comparison sample section 21.

When a test sample color comparison is to be carried out using the color comparison device of the above construction, a mode key 1a, exposed through the manipulable window 34, is first depressed to turn on the power source. Then, a specimen, for example, blood is applied to the test paper portion 51 of the test stick 5, and then a start key 1b is depressed to activate a timer which sets a predetermined reaction time (i.e., time required for the color reaction on test paper portion 51). When the timer stops its operation and the operator is notified by, for example, an audible beep, the test stick 5 is inserted into the stick insertion groove portion 13, with its test paper portion 51 first introduced thereinto. At this time, the test stick 5 is moved into the stick insertion inlet portion 34 in an inclined condition because of the provision of the bulged section 6. Therefore, the test stick 5 is flexed to produce a restoring force, and this restoring force is borne by the apex or peak of the bulged section 6 and the insertion inlet portion 35. The distal end of the test stick 5 is passed through the insertion inlet portion 35 while it is kept in the flexed condition, so that the distal end is brought into abutment against the stopper projection 37, thereby preventing a further advance of the test stick 5. In this condition, the color test paper portion 51 is exposed and viewed through the comparison window 33, and is disposed in proper registry and contact with the upper surface of the comparison color sample section 21. It is also held in position by its flexure.

Thus, the test stick 5 is passed through the insertion inlet portion 35 in the flexed condition because of the provision of the bulged section 6, and the restoring force produced by this flexing (i.e., a restoring force of the material of the test stick 5) is borne by the insertion inlet portion 35 so that the test stick is fixed. Therefore, even if the device body 1 is tilted during the time when the manipulable wheel 2 is rotated to bring different color shades on wheel 2 into registration with test paper portion 51, the test stick will not be accidentally disengaged from the device body, thereby ensuring a stable color comparison operation.

As described above, in the present invention, the stick insertion groove portion is provided with the stick-fixing bulged section, and therefore the test stick is moved into the stick insertion inlet portion in an inclined condition due to the bulged section, so that the test stick is flexed. This flexed condition is maintained by the bulged section and the insertion inlet portion to thereby positively fix the test stick. Therefore, the test stick in its inserted condition is firmly fixed, and so long as an outward pulling force is not applied to the test stick, the test stick will not be accidentally disengaged from the device body during the color comparison operation.

While a preferred embodiment of the invention has been described and illustrated it should be apparent that many modifications can be made without departing from the spirit and scope of the invention. Accordingly, the invention is not limited by the foregoing description but is only limited by the scope of the appended claims.

We claim:
1. A color comparison device comprising:
   a casing unit having a comparison window for displaying a comparison color sample section mounted on a rotatable wheel wherein the wheel is rotatably fixed with a protruding display section of the casing unit;
   a test stick insertion groove portion formed in an upper surface of said casing unit at one end portion thereof, said insertion groove portion communicating with said comparison window so that a reagent portion of a test stick inserted into said insertion groove portion overlies said comparison color sample section in said comparison window;
   means for causing a test stick inserted into said insertion groove to be held in a flexed condition wherein said causing means comprises a bulged fixing section provided at said insertion groove and an inlet portion of said insertion groove portion, a test stick inserted into said insertion groove being held in a flexed condition by said bulged fixing section and said inlet portion of said insertion groove.

* * * * *